United States Patent [19]

Babcock

[11] 3,957,186
[45] May 18, 1976

[54] METHOD AND APPARATUS FOR TEARING SECTIONS FROM A WEB

[75] Inventor: Donald Babcock, Oak Lawn, Ill.

[73] Assignee: Johnson & Johnson, New Brunswick, N.J.

[22] Filed: Mar. 10, 1975

[21] Appl. No.: 556,998

Related U.S. Application Data

[63] Continuation-in-part of Ser. No. 377,352, July 9, 1973, abandoned.

[52] U.S. Cl. ................................. 225/3; 225/101; 225/106
[51] Int. Cl.² ......................................... B26F 3/00
[58] Field of Search ............. 225/1, 3, 93, 100, 101, 225/106

[56] References Cited
FOREIGN PATENTS OR APPLICATIONS
423,443    4/1967    Switzerland ....................... 225/101

*Primary Examiner*—Othell M. Simpson
*Assistant Examiner*—Leon Gilden

[57] ABSTRACT

A web of fibers is continuously fed between a rotating tearing apparatus where the web is torn into sections without causing compression of the fibers at the tear line. The tearing apparatus is comprised of two opposed rotating pairs of web holding means or jaws which receive and engage the web. To tear the web, the leading jaw of each pair is angularly displaced away from the corresponding trailing jaw and then returned to a juxtaposed position relative to the trailing jaw. Preferably the jaws are provided with arcuate working surfaces which may be tipped with a resilient material to increase jaw life and to improve the holding characteristics thereof for webs of contoured cross section.

12 Claims, 10 Drawing Figures

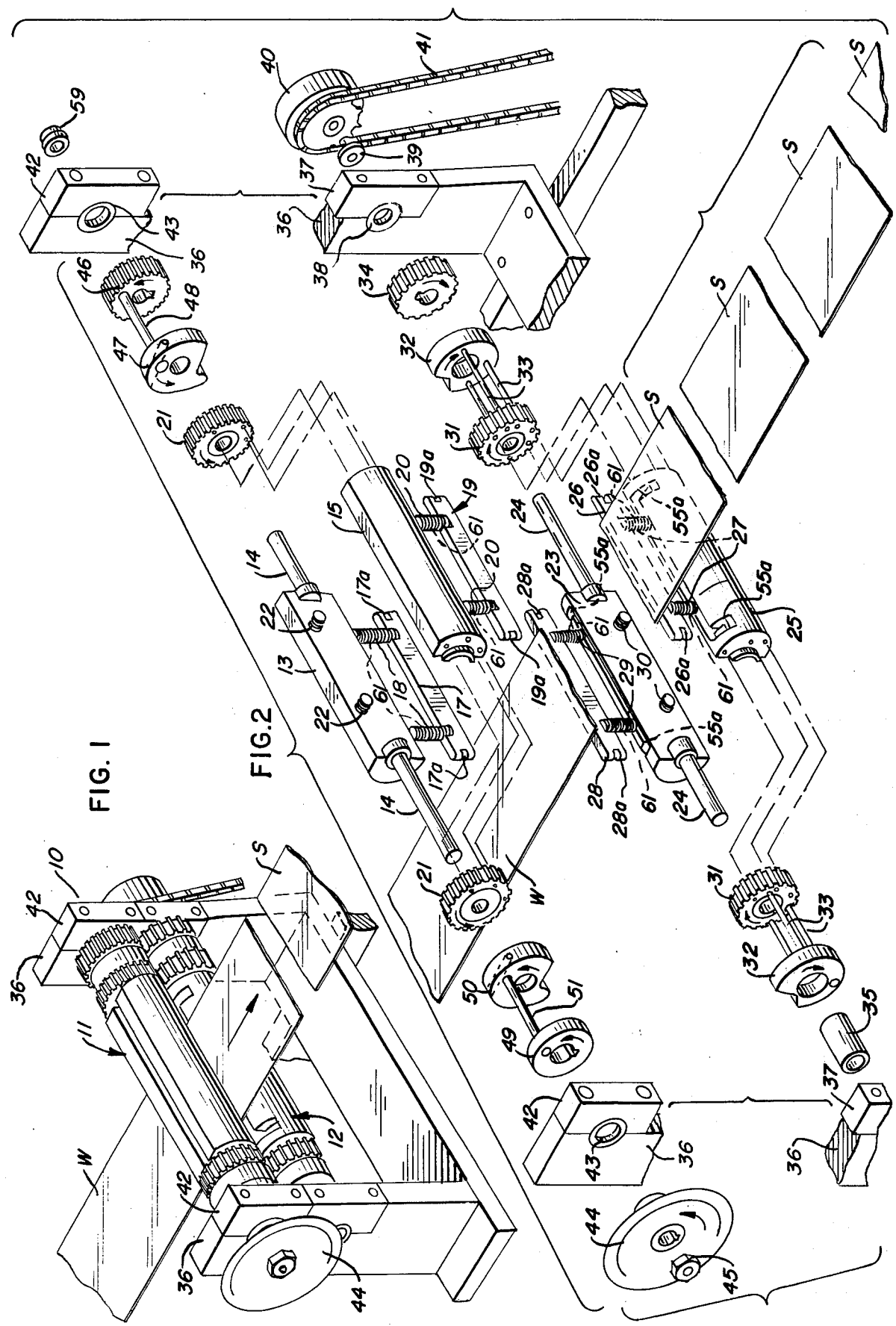

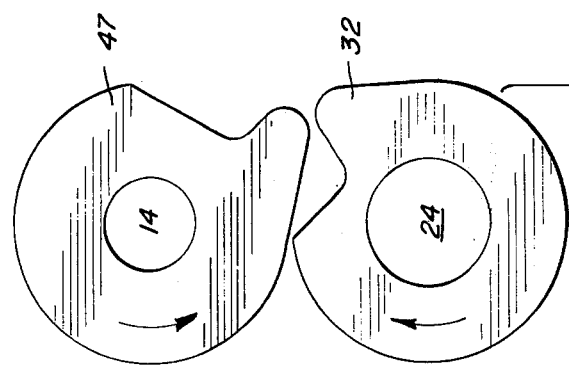
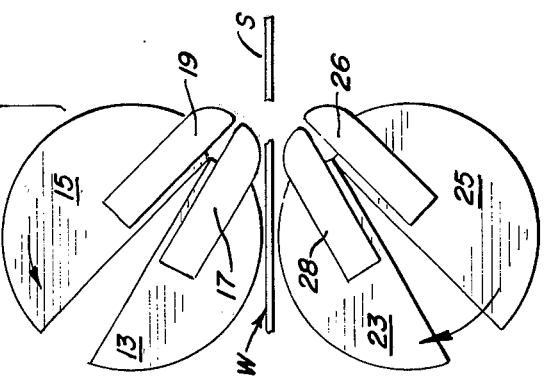
FIG. 3c
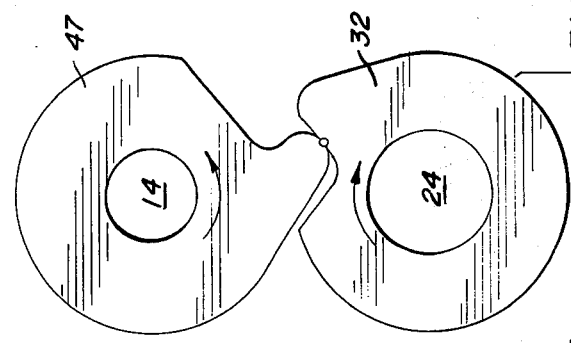
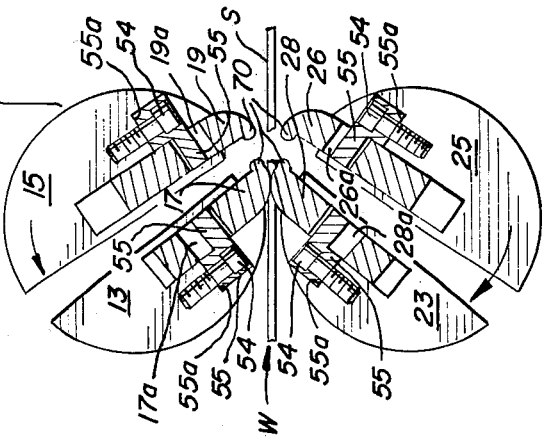
FIG. 3b
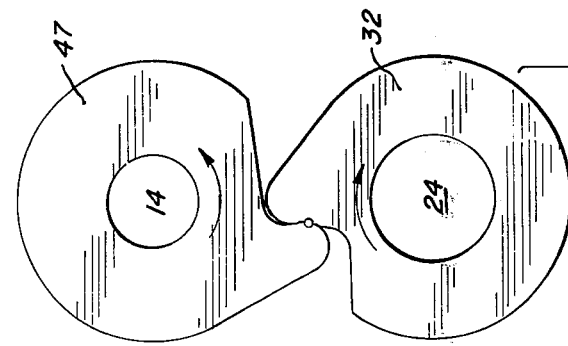
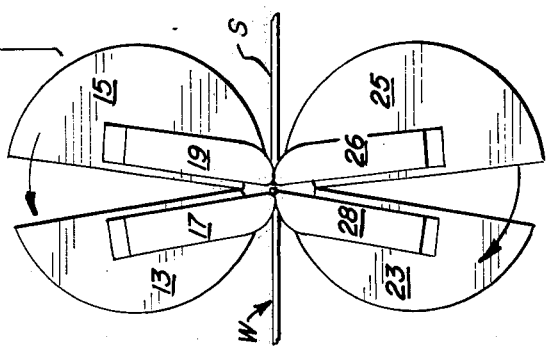
FIG. 3a
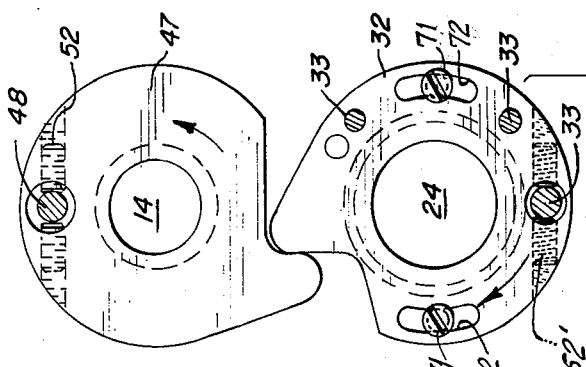
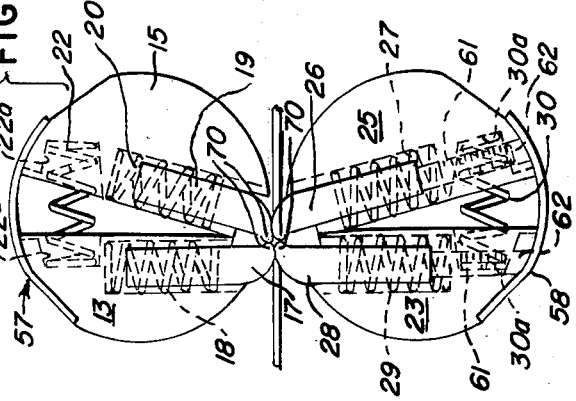
FIG. 3

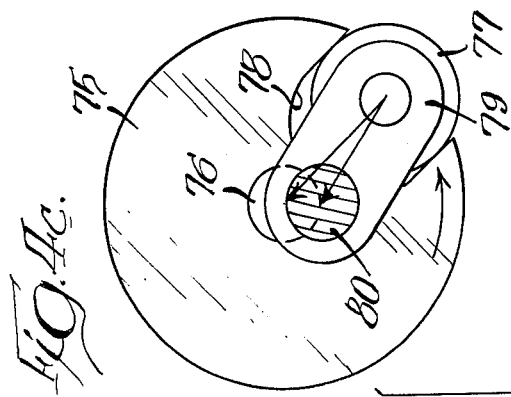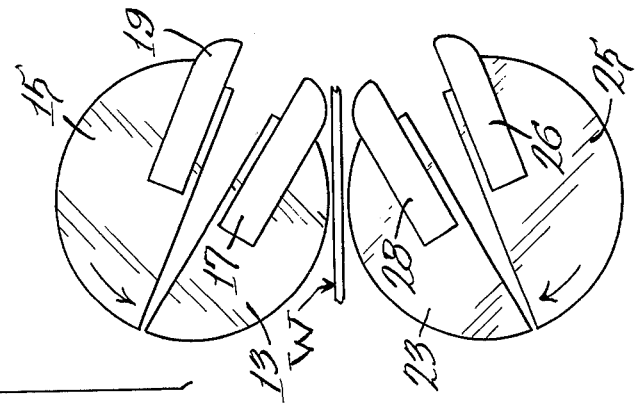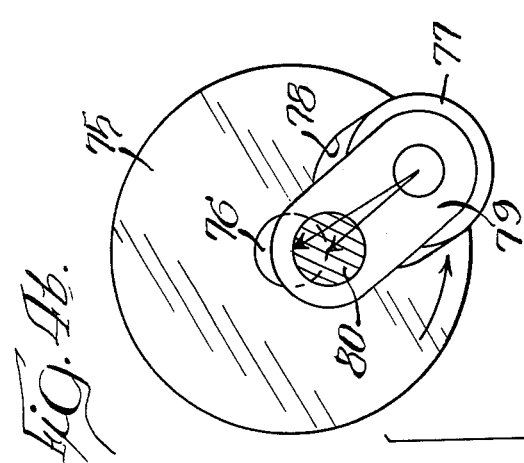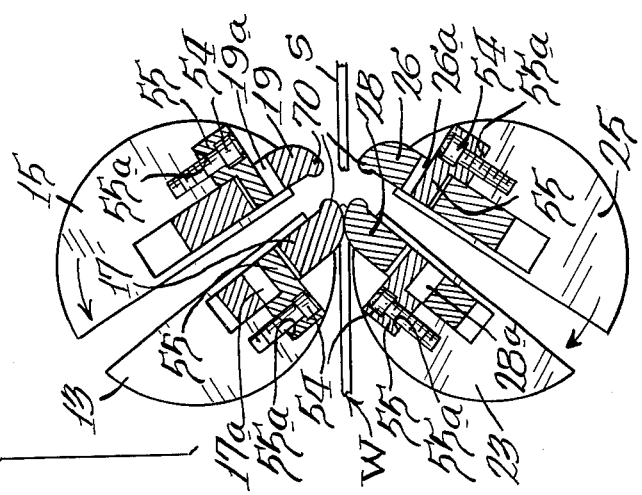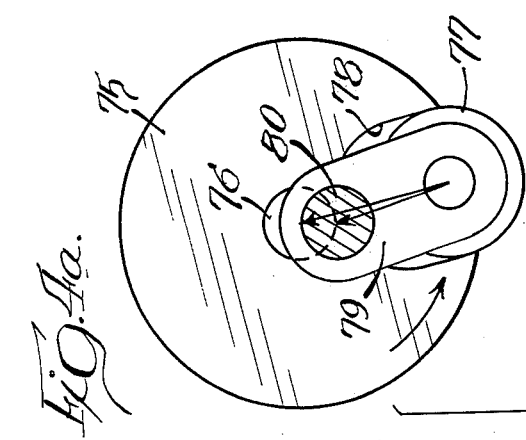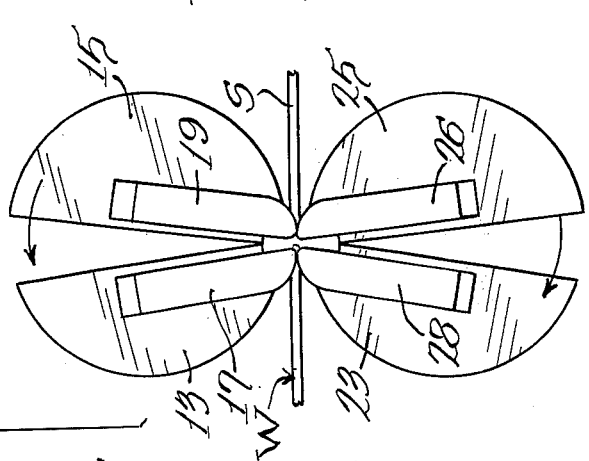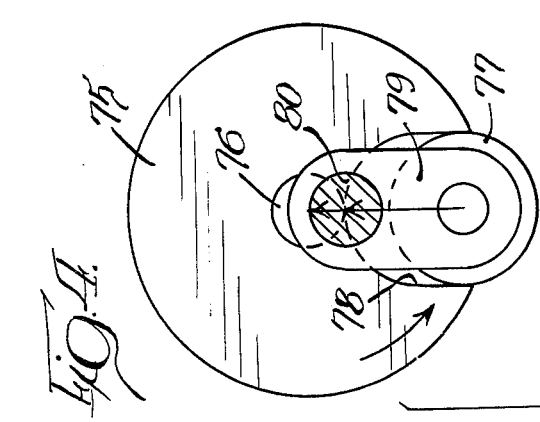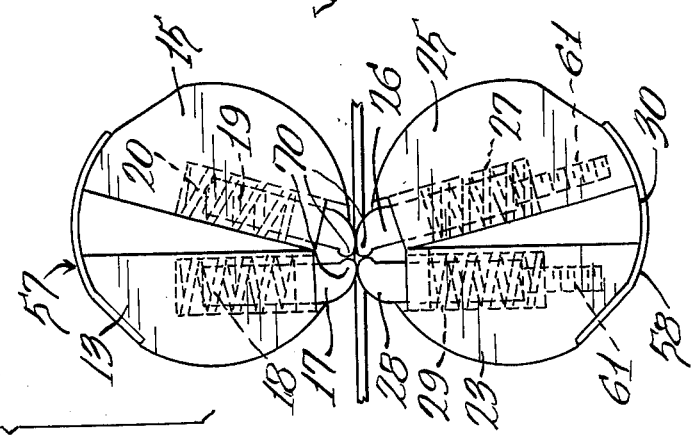

METHOD AND APPARATUS FOR TEARING SECTIONS FROM A WEB

CROSS-REFERENCE TO RELATED APPLICATIONS

This application is a continuation-in-part of U.S. Ser. No. 377,352; filed on July 9, 1973 now abandoned.

BACKGROUND OF THE INVENTION

The present invention relates to fiber web processing and more particularly to devices for severing air laid webs.

In the formation of web sections from air laid webs, any permanent compression of the fibers will result in increased wickability, or preferential absorptivity along the compressed fibers due to the reduction in effective capillary radius of these fibers. This result may be most disadvantageous in the formation of diaper web sections since liquid migration will be along the line of densification. If this line occurs at an edge, as where the section is cut with a knife edge, there is a strong tendency for any liquid coming into contact with the densification line to be drawn into and concentrated at the edge. Accordingly, there exists a need for web-tearing devices which are capable of partitioning a web into segments without producing undesirable lines of densification. Both the commonly assigned Shepherd application, U.S. Ser. No. 377,372, filed July 9, 1973, and the present specification disclose devices which tear a web to form sections without creating densification at the tear line.

The aforementioned Shepherd application discloses apparatus for tearing an intermittently fed web wherein a pair of juxtaposed opposing jaws operate transversely on a web to form sections. Each pair of jaws consists of a first jaw and a second biased hinged jaw so that after the jaws grip the web, the first jaws hold the web and the second jaws are displaced from their juxtaposed position, thus tearing the web transversely. The apparatus and method of the present invention is directed to severing web sections from a continuously fed web at high production rates.

German Patent No. 1,252,050 to Hesser shows a device for separating cardboard sections defined by lines of weakening from a continuous strip of cardboard. The section to be severed from the strip is held between a rubber bar and an underlying roller while the rest of the continuous strip is moved rearwardly by the action of a single, slidably-mounted segment of the underlying roller. In contradistinction thereto, in the present apparatus a continuously moving web is fed between two opposed rotatable pairs of web engaging jaw members and is gripped by the trailing set of jaw members while the leading set of jaw members is accelerated away from the trailing set to sever a web section and to move the severed section away from the web.

SUMMARY OF THE INVENTION

The present web-tearing apparatus comprises a frame; tearing means rotatably mounted in the frame and including two opposed, rotatable pairs of web-engaging members each pair comprising a trailing jaw member and a juxtaposed leading jaw member; driving means for simultaneously rotating the web-engaging members in opposite directions relative to each other; and accelerating means for shifting the juxtaposed leading jaw members substantially simultaneously away from the respective trailing jaw members and in the general direction of web movement between the opposed, rotatable pairs of web-engaging members.

The jaw members can be mounted in the curved portions of two pairs of cylinder segments geared to rotate together in the direction of web feed and timed so that the corresponding jaw members in each pair are simultaneously brought into engagement with and grasp the web. The engagement of the jaw members with the web corresponds with the advancement of the portion of the web to be torn to form a section.

As the web is fully engaged by the jaws, a displacing or accelerating means, such as a cam or the like, displaces one cylinder segment of each pair relative to the other cylinder segment so that the web is torn. The displacing means can be timed to release the displaced cylinder segments which can then be returned to the non-displaced position by a biasing means as the pairs continue to rotate, thus placing the apparatus in condition for another tearing operation. Alternately, by means of continuous camming or elliptical gearing one cylinder segment can be continuously moved away from each other during first $\pi$ radians of rotation and then moved back toward each other during the next $\pi$ radians of rotation.

To provide for the aforementioned rotation and displacement, the cylinder segments are operatively connected in pairs, and optionally biased, so that the jaws of each pair are juxtaposed while the web is being advanced. One cylinder segment of each pair is rotatably mounted by end shafts to the frame. The cylinder segment pairs are mounted in alignment, and the web is continuously fed between them.

A web-tearing apparatus of the present invention may use jaws having working edges which are either hard or resilient. Hard edged jaws will provide good holding strength and create a transverse densification line at the engagement line to cooperate with preformed longitudinal densification lines to form transfer paths for directing liquid migration from one longitudinal densification line to another. Resilient edged jaws, such as jaws with rubber tips, will not create transverse densification lines at the engagement lines due to lesser loading than hard edged jaws. However, resilient edged jaws will give better wear characteristics to other elements of the mechanism, and provide longer life for such elements.

A feature of this invention is that web sections are severed from a continuously moving web without compression of the fibers at the severance line. If desired, the web section may be formed with a transverse densification line near the severance line by using web holding means having hard, non-deformable working edges for engaging the web. In either case, however, the stressing and tearing action substantially eliminates any preformed densified layer or thickened portions at the ends of the sections torn from the web.

BRIEF DESCRIPTION OF THE DRAWINGS

For a more complete understanding of the invention, reference is made to the accompanying drawings in which:

FIG. 1 is a perspective view of an apparatus embodying the present invention;

FIG. 2 is an exploded perspective view of an apparatus embodying the present invention;

FIGS. 3–3c are elevation views partially in cross section illustrating the action of the web tearing means with intermittent camming and demonstrating various timing phases during the tearing cycle; and FIGS. 4–4c are elevation views similar to FIGS. 3–3c and illustrating continuous camming for actuating the web tearing means.

DETAILED DESCRIPTION OF PREFERRED EMBODIMENTS

While this invention is susceptible of embodiment in many different forms, there is shown in the drawings and will herein be described in detail preferred embodiments of the invention with the understanding that the present disclosure is to be considered as an exemplification of the principles of the invention and is not intended to limit the invention to the embodiments illustrated. Still other variations and rearrangements of parts are possible within the spirit and scope of this invention.

The apparatus of the present invention is specified in its entirety by 10, FIG. 1, and is comprised of an upper pair of semi-circular cylinder segments 11 and a lower pair of semi-circular cylinder segments 12 which rotate in the direction of web feed, and engage and tear the web W into sections S. One semi-circular cylinder segment 13 and 23 of each pair is provided with web engaging jaws 17 and 28, respectively, and with end mounted shafts 14 and 24, respectively, whereby the pairs of the semi-circular cylinder segments are rotatably mounted in the upright portions of the frame 36. The semi-circular cylinder segment shafts 14 are journaled in frame 36 by bushings 43 and mounting blocks 42. The ends of the shafts 14 are positioned in the bushings 43 by the collar 52 at one end, and a keyed handwheel 44 and nut 45 at the other end. Handwheel 44 is used to align the pairs of semi-circular cylinders 11 and 12 with the web W prior to start up. The semi-circular cylinder segment shafts 24 are rotatably mounted in frame 36 by bushings 38 and mounting blocks 37. One lower shaft 24 is connected to a safety clutch 40 through spacer 39, and is driven by a prime mover (not shown) connected thereto by chain 41.

The shaft-mounted semi-circular cylinder segments 13 and 23 are referred to as the trailing semi-circular cylinder segments. The other juxtaposed semi-circular cylinder segments 15 and 25, referred to as the leading semi-circular cylinder segments, are also provided with web-engaging jaws 19 and 26, respectively. During web engagement, the leading semi-circular cylinder segments 15 and 25 are angularly accelerated and displaced simultaneously relative to the trailing semi-circular cylinder segments 13 and 23 to stress and tear the web by the action of the respective web-engaging jaws. This displacement can be provided for by mounting the leading semi-circular cylinder segments 15 and 25 on the shafts 14 and 24, respectively, by two sets of gears 21 and 31, which are fixedly attached thereto and are free-running on their respective shafts 14 and 24. The gears 21 and 31 align the semi-circular cylinder segments of each pair with their straight portions juxtaposed, and provide for conjoint movement of the leading semi-circular cylinder segments 15 and 25 during the tearing cycle, as will be discussed in greater detail below. Compression springs 22 and 30 (FIGS. 2 and 3) are located in recesses 22a and 30a, and bias the opposing edges of the juxtaposed semi-circular cylinder segments of each pair together while providing clearance spaces to accommodate the angular displacement of the leading semi-circular cylinder segments 15 and 25 during the tearing cycle.

Each semi-circular cylinder segment carries a spring-loaded jaw 17, 19, 26 and 28, having arcuate working surfaces, mounted in its curved surface on the side opposite the compression springs 22 and 30. As illustrated in FIGS. 3 and 3b, jaws 17, 19, 26 and 28 are spring-loaded by four respective sets of springs 18, 20, 27, and 29, and are retained in their respective semi-circular cylinder segments by tangs 55. The tangs 55 are secured to the semi-circular cylinder segments in recesses 55a by bolts 54. The jaws 17, 19, 26 and 28 are free to move relative to their respective semi-circular cylinder segment by slots 17a, 19a, 26a and 28a. As illustrated in FIG. 3, each jaw is provided with a pair of guide pins 61 positioned coaxially with compression springs 18, 20, 27 and 29. Guide pins 61 are slidable in guide slots 62 to provide proper alignment of the jaws as they move in and out during the tearing cycle.

The paired semi-circular cylinder segments 11 and 12 are driven in the direction of web feed through a system of gears. Gear 34 is keyed to the driven lower right shaft 24, and drives the gear 46 keyed on the upper right shaft 14. The meshing of gears 34 and 46 provides for constant angular velocity of the trailing semi-circular cylinder segments 13 and 23 during all operationg cycles. It will be appreciated that during the normal web feed cycle rotation, the leading semi-circular cylinder of each pair rotates at the same angular velocity as the trailing semi-circular cylinder due to the contact between each semi-circular cylinder through the springs 22 and 30 and jaw juncture line as illustrated in FIGS. 3 and 3c.

Displacement of the leading semi-circular cylinder segments 15 and 25 is accomplished through a system of gears which are cammed during web engagement to displace the leading semi-circular cylinder segment relative to the trailing semi-circular segments 13 and 23. Gear 46 is attached to cam 47 by an arm 48 which is adjustably secured to the cam 47 by means of a chord positioned adjustment screw 52, FIG. 3, to provide for the timing, advancement and retardation of the cam lobe. A keyed hub 49 is axially mounted to the left upper shaft 14 and is similarly mounted to cam 50 by arm 51 and adjustment screw 52. Corresponding cams 32 are mounted to the lower shaft gears 31 by multiple connection arms 33, and are free running on the lower shafts 24. Cams 47 and 50 contact cams 32 during the tearing cycle to displace the leading semi-circular cylinder segments 15 and 25 and jaws 19 and 26 during jaw engagement of the web to tear the web. A spacer 35 is provided on the left hand lower shaft 24 for proper alignment of the shaft elements.

Curved dust covers 57 and 58, FIG. 3, are attached to the trailing semi-circular cylinder segments 13 and 23 and extend across the juncture gap between the flat surfaces of the semi-circular cylinders. The dust covers 57 and 58 are slidable on the curved surface of the leading semi-circular cylinder segments 19 and 25 to accommodate their movement during the tearing operation.

With reference to FIGS. 3 to 3c, the operation of the present invention is as follows. The web of fibers W is fed between the pairs of semi-circular cylinders 11 and 12 by feed means (not shown). As the web is fed, the pairs of semi-circular cylinder segments 11 and 12 are rotated by the prime mover in the direction of web feed. During the feed cycle, jaws 17 and 19 as well as 26 and 28 are held juxtaposed (FIG. 3) by the action of springs 22 and 30 disposed from the flat interfaces between the semi-circular cylinder segments. The time for one complete rotation of the pairs of jaws corresponds to the time for feeding a length of the web section S to be severed through tearing apparatus 10. After the desired length of web has been fed between the pairs of semi-circular cylinder segments 11 and 12, leading jaws 19 and 26 mounted in the leading semi-circular cylinder segment engage the web W. Almost simultaneously therewith, the trailing jaws 17 and 28 engage web W so that the web is fully grasped and held between the jaws as it is continuously fed. As illustrated in FIG. 3, when the trailing jaws 17 and 28 grasp the web W, the cam lobes of the upper cams 47 and 50 contact the lobes of the lower cams 32. As the upper and lower shafts continue rotating, the upper lobe cams 47 and 50 cause the leading semi-circular cylinders to be angularly accelerated due to the increased radial distance between the points of contact on the lobe cams, as illustrated in FIGS. 3a and 3b. This angular acceleration causes jaws 19 and 26 to be angularly displaced from their normal positions (FIGS. 3 and 3c). As the jaws 19 and 26 are displaced, springs 22 and 30 are compressed to accommodate the angular movement of the leading semi-circular cylinders 15 and 25. Due to the increased longitudinal stress generated by this displacement, the web W is torn transversely while being held by jaws 17, 19, 26 and 28. After lobe cams 47 and 50 have rotated past the contact apex, the lobes disengage (FIG. 3c) and compression springs 22 and 30 cause the leading semi-circular cylinder segments 15 and 25, and corresponding jaws 19 and 26, to return to their biased position in contact with trailing jaws 17 and 28. As the jaws continue to rotate, the web continually advances and the tearing operation is repeated.

Instead of intermittent camming, the leading jaw members can also be continuously shifted away from the trailing jaw members and subsequently returned to the aforesaid juxtaposed position relative to the trailing jaw members during each operating cycle. Such an arrangement is illustrated in FIGS. 4–4c where the same jaw members as shown in FIGS. 3–3c are continuously accelerated and decelerated by means of variator plate 75 fixedly mounted on drive shaft 76, which is driven through suitable gearing by the prime mover, and cam follower 77 received in radial camming slot 78 in variator plate 75. Cam follower 77 is rotatably mounted at one end of arm 79 the other end of which is fixedly attached to shaft 80 so that as shaft 80 is turned cam follower 77 orbits thereabout. The distal end of shaft 80 can be connected in any convenient manner to drive gears 31 (FIG. 2) which are fixedly mounted to leading semi-cylindrical jaw carrier segment 25 as discussed hereinabove. Variator plate drive shaft 76 can be driven independently or by means of appropriate gearing from gear 34, as desired. Variator plate drive shaft 76 and shaft 80 are parallel to each other, however, the respective longitudinal axes thereof are spaced from one another, as shown in FIGS. 4–4c.

As variator plate 75 is rotated through first and second quadrants of each operating cycle, i.e., during the first half of each operating cycle, cam follower 77, and thus shaft 80, are accelerated and leading jaw members 19 and 26 are shifted away from respective trailing jaw members, thereby severing a section from the web. During third and fourth quadrants of rotation by variator plate 75, however, i.e., the second half of the operating cycle, cam follower 77 is decelerated so that both the leading and trailing jaw members travel at substantially the same linear speed when the jaw members are about to engage the web. The same kind of continuous accelerating and decelerating motion for leading jaw members 19 and 26 can also be obtained using a combination of coacting elliptical gears rather than a combination of a slotted variator plate with a cam follower received therein.

As has been indicated, during the severance of sections S from fiber webs, any permanent compression of the fibers at the tear line will result in densification lines which increase liquid migration along the line due to the reduction in effective capillary radius of the fibers. In one embodiment of the present invention, FIGS. 3 and 3b, the jaws 17, 19, 26 and 28 are formed with resilient tips 70, such as rubber, that prolong the life of other elements, such as the cams, bearings and springs. Moreover, where the web to be torn is contoured in cross section rather than rectangular, the use of resiliently tipped jaws provides better grasping qualities.

In order to compensate for the rectangular shape of web sections S, some webs are preformed with a densified layer either alone or in combination with longitudinal thickened lines to increase liquid migration in the longitudinal direction thereby more fully utilizing fiber absorption, e.g., Burgeni U.S. Pat. No. 3,017,304, and commonly assigned Repke application Ser. No. 396,242 filed Sept. 11, 1973. When these types of webs are severed into sections, it is desirable to eliminate the densified layer and longitudinal thickened portions at the ends of the sections so that there will be minimum liquid migration thereto. The apparatus of the present invention due to its web stressing characteristics during the tear cycle substantially eliminates the densified layer and thickened portions which may have been preformed in the web, and thus reduces liquid migration to the ends of the sections.

In conjunction with this stressing characteristic, a second embodiment of the present invention may be employed in which the jaws are not tipped with a resilient material, as in FIG. 3a. The use of the hard jaws provides greater grasping load and creates a transverse densification line at the web engagement due to the pressure exerted on the web by the jaws. The transverse densification line created at each engagement line of the section will cooperate with the longitudinal thickened portions to form transfer paths between the longitudinal thickened portions.

In order to give the transverse densified lines the desired degree of permanence, the web is sprayed with water, as is known in the art, e.g., Burgeni U.S. Pat. No. 3,017,304, to provide inter-fiber bonds between the fibers in the engagement area. This spraying may be done during web formation before the web is conveyed to a tearing apparatus of the present invention, or as the web is conveyed to the tearing apparatus.

I claim:

1. Apparatus for severing separate sections from a web which is continuously fed therethrough comprising:
    frame means;
    tearing means rotatably mounted in the frame means and including two opposed rotatable pairs of web-engaging, resiliently-mounted members, each pair having a trailing jaw member and a juxtaposed leading jaw member pivotally mounted with respect to the driven jaw member;

driving means simultaneously rotating said pairs of web engaging members in opposite directions relative to each other so that said opposed, resiliently-mounted members engage said web at about the same time; and accelerating means shifting said juxtaposed leading jaw members substantially simultaneously away from the respective trailing jaw members and in the general direction of web movement when the trailing jaw members engage the web therebetween while the web-engaging extremities thereof travel at substantially the same linear speed as the web, thereby severing a portion of said web and moving said severed portion away from said web.

2. Apparatus as set forth in claim 1, wherein each of said web engaging jaw members is positioned transversely across said web, and wherein the web contacting surfaces of each pair of web engaging jaw members are resiliently biased toward each other.

3. Apparatus as set forth in claim 1, wehrein each of said web engaging jaw members is resiliently mounted within a recess in a rotatable housing, and wherein the housings for each pair of web engaging members are in complementary juxtaposition to each other.

4. An apparatus as set forth in claim 3 wherein a spring resiliently biases said housings toward each other.

5. Apparatus as set forth in claim 2 wherein said web contacting surfaces are arcuate.

6. Apparatus as set forth in claim 5 wherein said arcuate contacting surfaces are formed of flexible material.

7. Apparatus as set forth in claim 1 wherein said accelerating means is adapted to continuously shift said juxtaposed leading jaw members first away from and then toward the respective trailing jaw members during each operating cycle.

8. Apparatus as set forth in claim 1 wherein said accelerating means is adapted to intermittently pivot said juxtaposed leading jaw members away from the respective trailing jaw members and wherein a bias means is situated between each set of leading and trailing jaw members urging said leading and trailing jaw members in each set toward one another.

9. An apparatus for severing separate sections from a web comprising: frame means; tearing means rotatably mounted relative to said frame means and defining a web feed path, said tearing means including two pairs of transversely disposed spaced semi-cylindrical members located in juxtaposition on opposite sides of a web adapted to be fed therebetween and supporting resiliently mounted web holding jaw means, and one member of each pair being a driven member and the other member of said pair being pivotally mounted in said frame means with respect to the driven member; means for continuously rotating said pairs of semi-cylindrical members in opposite directions relative to each other; means operatively coupling each pair of semi-cylindrical members whereby the members of each pair rotate conjointly and including coupling gear means attached to the pivotally mounted members of each of said pairs and positioned and free running with respect to the driven members of each pair so as to enable each of said pivotally mounted members to rotate together with its respective frame mounted member and to be moved relative thereto during web-severing action; the web holding jaw means supported by one pair of semi-cylindrical members being positioned relative to the web holding jaw means of the other pair of semi-cylindrical members whereby, when the pairs of semi-cylindrical members are rotated, the web holding jaw means of each pair are periodically brought into concurrent engagement with said web; means biasing the semi-cylindrical members of each pair relative to each other whereby the web holding jaw means in each pair of semi-cylindrical members are placed in juxtaposition; and moving means for moving one of the semi-cylindrical members of one pair relative to the other semi-cylindrical member of said one pair substantially simultaneously on both sides of the web during engagement with the web to stress and sever a section of web; said moving means being comprised of cam means including drive cam means operatively mounted to rotate with one of the frame mounted semi-cylindrical members of one pair, and driven cam means fixedly positioned relative to the coupling gear means on the pivotally mounted semi-cylindrical member of the other pair whereby the action of said drive cam means is transmitted to each of said pivotally mounted members by said gear means, thereby to simultaneously move one web holding jaw means of each pair relative to the other web holding jaw means of each pair during engagement of the web to stress and sever a section of web.

10. A method of severing sections of predetermined length from a continuous fibrous web which comprises:

providing two opposed pairs of spaced, rotatable jaw members, continuously feeding the continuous fibrous web between said opposed pairs of jaw members while said jaw members are rotated together in the direction of web feed so that the web-engaging extremities of the jaw members travel at the same linear speed as the web, grasping the web between opposed sets of rotating jaw members, and substantially simultaneously accelerating the leading set of the rotating opposed web-engaging jaw members relative to the trailing set of the rotating opposed web-engaging jaw members while the web is held between said trailing set of opposed jaw members so as to sever a segment from said web and move the severed segment away from the web.

11. The method in accordance with claim 10 wherein the leading set of said rotating opposed web-engaging jaw members are intermittently accelerated relative to the trailing set of said rotating opposed web-engaging jaw members.

12. The method in accordance with claim 10 wherein the leading set of said rotating opposed web-engaging jaw members are continuously accelerated during the first half of each operating cycle relative to the trailing set of said rotating opposed web-engaging jaw members and are continuously decelerated during the second half of each operating cycle.

* * * * *